United States Patent [19]
Anton et al.

[11] Patent Number: 5,233,058
[45] Date of Patent: Aug. 3, 1993

[54] PARTIALLY FLUORINATED COMPOUNDS AND POLYMERS

[75] Inventors: Douglas R. Anton, Claymont; William B. Farnham, Hockessin; Ming-Hong Hung; Ronald J. McKinney, both of Wilmington, all of Del.

[73] Assignee: E. I. Du Pont de Nemours and Company, Wilmington, Del.

[21] Appl. No.: 780,374

[22] Filed: Oct. 21, 1991

Related U.S. Application Data

[60] Division of Ser. No. 450,351, Dec. 11, 1989, abandoned, which is a continuation-in-part of Ser. No. 223,867, Jul. 25, 1988, abandoned.

[51] Int. Cl.⁵ .................. C08D 317/34; C08D 317/42
[52] U.S. Cl. ........................ 549/450; 549/451; 549/455
[58] Field of Search ................ 549/450, 451, 454, 455

[56] References Cited

U.S. PATENT DOCUMENTS

| | | | |
|---|---|---|---|
| 2,554,786 | 5/1951 | McBee | 558/454 |
| 3,496,215 | 2/1970 | Drinkard et al. | 260/465.8 |
| 3,496,217 | 2/1970 | Drinkard et al. | 260/465.8 |
| 3,496,218 | 2/1970 | Drinkard et al. | 260/465.8 |
| 3,503,945 | 3/1970 | Kim | 526/245 |
| 3,544,618 | 12/1970 | Dorfman | 560/172 |
| 3,865,845 | 2/1975 | Resnick | 260/340.9 |
| 4,002,657 | 1/1977 | Jager | 260/408 |
| 4,535,175 | 8/1985 | Squire | 549/455 |
| 4,810,806 | 3/1989 | Krespan | 549/448 |
| 5,011,954 | 4/1991 | Hung et al. | 549/548 |

FOREIGN PATENT DOCUMENTS

| | | |
|---|---|---|
| 352718 | 1/1990 | European Pat. Off. |
| 1404744 | 5/1965 | France |
| 2126340 | 6/1972 | France |

OTHER PUBLICATIONS

R. T. Morrison and R. N. Boyd, Organic Chemistry, 3rd Ed (1973) p. 318 1002-3.
NISax+R. J. Lewis, Hawley's Condensed Chemical Dictionary, 11th Ed (1987) pp. 34, 35.
Grant & Hackh's Chemical Dictionary, 5th Ed. (1987) pp. 22, 412.
I. L. Knuyants et al. Russian Chemical Rev. 32, 461-476 (1963).
P. L. Coe et al. J. C. S. Perkisn I, 654-656 (1975).
P. Johncock et al. J. Polym. Sci. A. Polym. Chem. 24, 2033-2045 (1986).
Hackh's Chemical Dictionary, 4th Edition, McGraw-Hill, New York, 1969, p. 132.
Marks et al., J. Polymer Sci., 43:229 (1960).
Tolman et al., Adv. in Catalysis, 33:1 (1985).
Chem. Abstracts, vol. 60, No. 13, Jun. 22, 1964, abst. No. 15720g & Moore, J. Chem. Eng. Data 9(2), 251-4 (1964) & 7th Collective Index, vol. 56-65, (Ni-Phe), 1962-1966, pp. 15421s & 15422s.

*Primary Examiner*—Joseph L. Schofer
*Assistant Examiner*—Mark Nagumo
*Attorney, Agent, or Firm*—William H. Hamby

[57] ABSTRACT

Partially fluorinated compounds of specified formulas that are useful as chemical intermediates and monomers are disclosed. Partially fluorinated polymers prepared from one of these compounds are also disclosed. Fluoro-2,2-dimethyldioxolanes and copolymers thereof are further disclosed.

1 Claim, 1 Drawing Sheet

PARTIALLY FLUORINATED COMPOUNDS AND POLYMERS

CROSS-REFERENCE TO RELATED APPLICATION

This application is a division of application Ser. No. 07/450,351 filed Dec. 11, 1989, abandoned which is a continuation-in-part of U.S. Ser. No. 223,867, filed Jul. 25, 1988, now abandoned.

FIELD OF THE INVENTION

The present invention concerns partially fluorinated compounds which are useful as chemical intermediates or monomers. The invention further concerns partially fluorinated condensation polymers and dioxolanes.

BACKGROUND OF THE INVENTION

Fluorinated intermediates are employed in the synthesis of a variety of chemical compounds, such as partially fluorinated polymers. Novel fluorinated intermediates and polymers derived therefrom are of significant interest to the chemical industry.

Partially fluorinated condensation polymers are known in the literature, see. e.g., I. L. Knunyants, C. Li, and V. V. Shokina, Russ. Chem. Rev., 32:461 (1963), and the references described therein. These polymers generally have been made to obtain materials with improved thermo-oxidative stability and solvent resistance, as compared to nonfluorinated polymers.

Many partially fluorinated condensation polymers have been made with perfluoro diacids, $HOOC-(CF_2)_n-COOH$, as one component of the polymer, see, e.g., B. S. Marks & G. C. Schweiker, J. Polymer Sci. 43:229 (1960) wherein the synthesis of partially fluorinated polyamides containing perfluoro diacid units is disclosed. The polymers made from such perfluoro diacids, however, suffer from problems associated with the extreme hydrolytic instability of the perfluoroacyl functional groups. The strongly electron-withdrawing perfluoroalkyl group situated next to the carbonyl of the perfluoroacyl group activates the carbonyl to hydrolysis. It has been found that many of the resulting polymers hydrolyze in moist air.

P. Johncock, S. P. Barnett, & P. A. Rickard, J. Polymer Sci./Polymer Chem. 24:2033 (1986) disclose the synthesis of a diacid wherein the fluoroalkyl chain is separated from the acyl group by a methylene spacer, $HOOC-CH_2-(CF_2)_3-CH_2-COOH$. Although polyesters made with this diacid are more hydrolytically stable than those made from perfluoro diacids, these compositions still hydrolyze under mild conditions. This acid also suffers from the ready loss of two moles of hydrogen fluoride from the molecule.

P. L. Coe., N. E. Milner & J. A. Smith, J. Chem. Soc./Perkin I 654 (1975) disclose use of perfluoroalkylcopper compounds to form certain polyfluoroalkyl-substituted acids and alcohols. These compounds are said to be of practical interest as surfactants. In one reaction, (1E,6E)-3,3,4,4,5,5-hexafluoro-1,7-di-iodohepta-1,6-diene was reacted with copper(I) cyanide. Hydrolysis of the resulting unsaturated dinitrile yielded a diacid that was hydrogenated to give $HOOC-CH_2CH_2-(CF_2)_3-CH_2CH_2-COOH$.

U.S. Pat. No. 3,496,215 discloses hydrocyanation of unsaturated compounds using as a catalyst a compound of the structure $Ni(PXYZ)_4$ wherein X is OR; Y and Z are R or OR; and R is an alkyl or aryl radical of up to 18 carbon atoms. U.S. Pat. No. 3,496,217 discloses hydrocyanation of nonconjugated ethylenically unsaturated organic compounds using certain nickel complexes as a catalyst and certain zinc containing compounds as promoters. U.S. Pat. No. 3,496,218 discloses hydrocyanation of nonconjugated ethylenically unsaturated organic compounds using certain nickel complexes as catalysts and certain organoboron compounds as promoters.

C. A. Tolman et al., Adv. in Catalysis, 33:1 (1985) disclose homogeneous nickel-catalyzed olefin hydrocyanation, as well as unpromoted hydrocyanations of monoolefins and hydrocyanations promoted with Lewis acids.

The synthesis of compositions of the present invention starts with bis-2,2-trifluoromethyl-4,5-difluorodioxole,

This dioxole was claimed by Resnick in U.S. Pat. No. 3,865,845.

SUMMARY OF THE INVENTION

The present invention provides compounds of the formula $$H_2C=CH-R_f-CH_2CH_2-Y \quad (1)$$

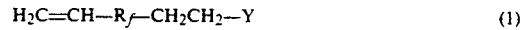

wherein Y is selected from the group consisting of $-CN$, $-CH_2NH_2$, $-COOH$, $-CH_2OH$, $-CH_2N=C=O$, $-CONH_2$, $-CHO$, $-COCl$, and $-COOR$, wherein R is $C_nH_{2n+1}$ and n is an integer from 1 to 10, inclusive; and $R_f$ is a fluorinated divalent organic radical selected from the group consisting of linear, branched, carbocyclic, and mixtures thereof having from 1 to about 40 carbon atoms.

The invention additionally provides compounds of the formula $$Y'-CH_2CH_2-R_f-CH_2CH_2-Y' \quad (2)$$

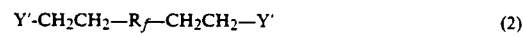

wherein Y' is independently selected from the group consisting of $-CN$, $-CH_2NH_2$, $-CH_2OH$, $-CH_2N=C=O$, $-CONH_2$, $-CHO$, $-COCl$, and $-COOR$, wherein R is $C_nH_{2n+1}$ and n is an integer from 1 to 10, inclusive; and $R_f$ is as defined above.

Compound (2) can be employed in a condensation type of polymerization reaction to prepare polymers (A) and (B) of this invention. Polymer (A) can be either polymers comprising 100 mole percent of at least one independently selected repeating unit of the formula $$-[X-CH_2CH_2-R_f-CH_2CH_2-X-X'-Z-X']- \quad (3)$$

wherein X is independently selected from the group consisting of $NHCH_2-$, $OCH_2-$, $-C(=O)$, and $-CH_2NH(C=O)$, X' is independently selected from the group consisting of $NH-$, $O-$, and $-C(=O)$, provided that when X is $NHCH_2-$ or $OCH_2-$, X' must be $-C(=O)$, and also provided that when X is $-C(=O)$ or $-CH_2NH(C=O)$, X' must be $NH-$ or $O-$; Z is any divalent organic radical; and $R_f$ is as defined above; or copolymers comprising from 1 to 99 mole percent of at least one independently selected repeating unit of formula (3) and from 99 to 1 mole percent of at least one independently selected repeating unit of the formula

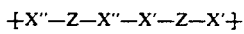  (4)

wherein X' and Z are as defined above, and Z is a independently selected, and X" is independently selected from the same group as X, provided that when X' is —C(=O), X" must be NH— or O—, and also provided that when X' is NH— or O—, X" must be —C(=O). In the nomenclature for polymer (A), the dashes found in the X, X', and X" divalent groups indicate the side of the group that is attached either to —CH$_2$CH$_2$—R$_f$—CH$_2$CH$_2$— in repeating unit (3) or to Z in repeating units (3) and (4).

Polymer (B) can be either polymers comprising 100 mole percent of at least one independently selected repeating unit of the formula

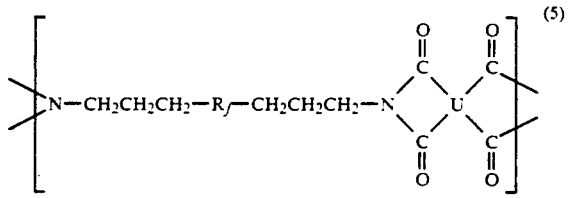  (5)

wherein U is any tetravalent organic radical and R$_f$ is as defined above; or copolymers comprising from 1 to 99 mole percent of at least one independently selected repeating unit of formula (5) and from 99 to 1 mole percent of at least one independently selected repeating unit of the formula

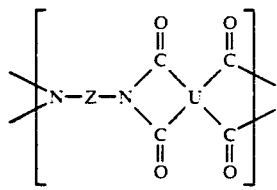  (6)

wherein U and Z are as defined above.

The invention also includes dioxolanes of the formula

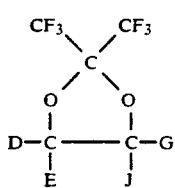

wherein D, E, G and J are:

| D  | E  | G  | J  |
|----|----|----|----|
| Cl | I  | Cl | Cl |
| Br | H  | Br | Cl |
| Br | Cl | Br | Cl |
| F  | F  | Cl | Cl |
| F  | I  | F  | I  |
| F  | I  | F  | Br |

-continued

| D | E | G | J |
|---|---|---|---|
| F | I | F | Cl |
| F | I | F | F |
| F | Br | F | F |
| F | CH$_2$CH$_2$I | F | CH$_2$CH$_2$I |
| F | CH$_2$CH$_2$I | F | F |
| F | CH$_2$CH$_2$I | F | Cl |
| F | CH$_2$CH$_2$I | F | Br |
| F | CH=CH$_2$ | F | CH=CH$_2$ |
| F | CH=CH$_2$ | F | F |
| F | CH=CH$_2$ | F | Cl |
| F | CH=CH$_2$ | F | Br |
| F | COOH | F | F |
| F | COOH | F | Cl |
| F | COOH | F | Br |
| F | COCl | F | F |
| F | COF | F | F |
| F | CH$_2$CH$_2$CH$_2$NH$_2$ | F | CH$_2$CH$_2$CH$_2$NH$_2$ |
| H | CH=CH$_2$ | H | CH=CH$_2$ |
| H | CH$_2$CH$_2$CN | H | CH$_2$CH$_2$CN |
| H | CH$_2$CH$_2$CH$_2$NH$_2$ | H | CH$_2$CH$_2$CH$_2$NH$_2$ |

Also included in the invention as new compositions of matter are

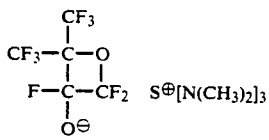

and

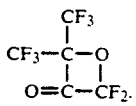

The invention further includes copolymers of tetrafluoroethylene with the above described dioxolane wherein D, E, G, and J are:

| D | E | G | J |
|---|---|---|---|
| F | CH=CH$_2$ | F | CH=CH$_2$ |
| H | CH=CH$_2$ | H | CH=CH$_2$ |
| F | CH=CH$_2$ | F | F |
| F | CH=CH$_2$ | F | Cl |
| F | CH=CH$_2$ | F | Br |

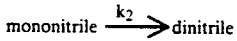

Figure 1:
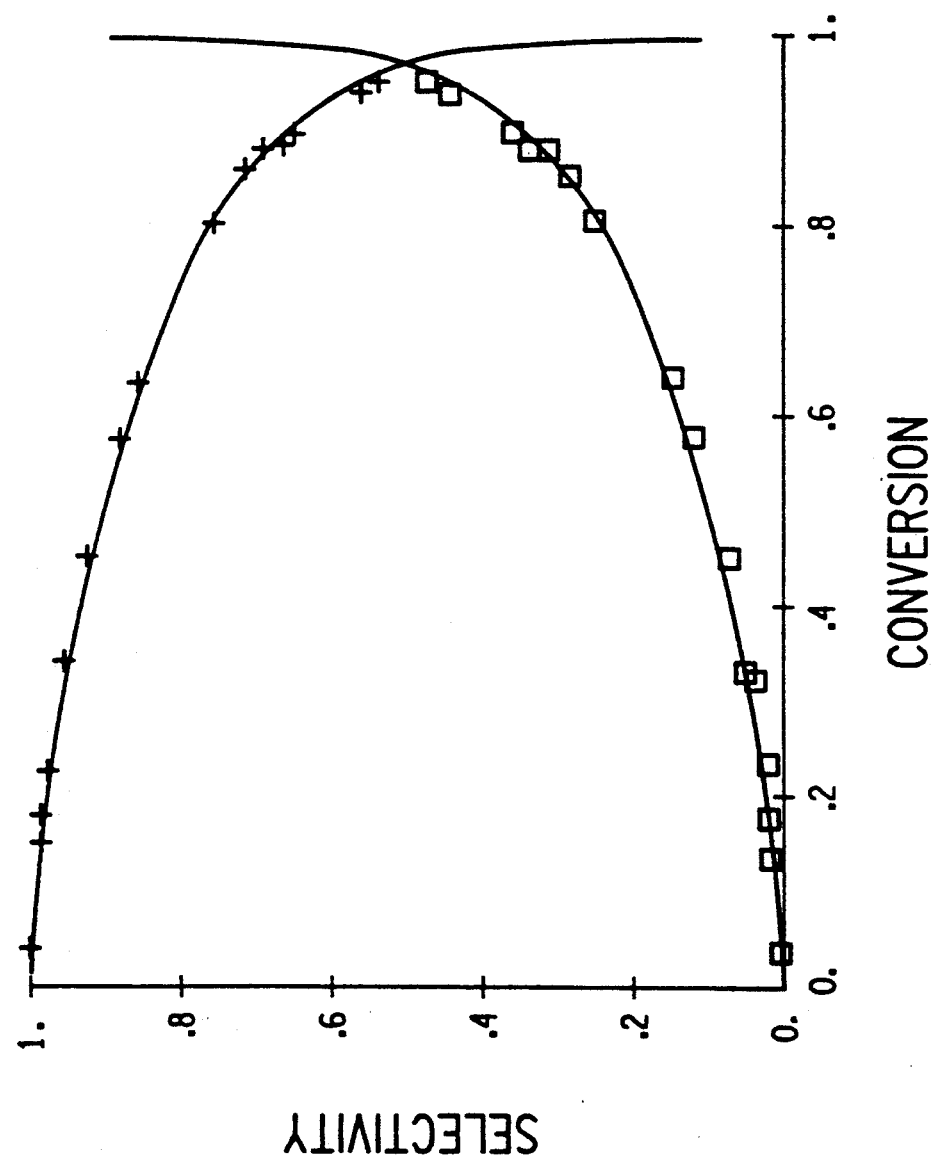
FIG. 1 plots the conversion of CH$_2$=CH—CF$_2$CF$_2$—CH=CH$_2$ against the selectivity to mononitrile and dinitrile. This shows that the hydrocyanation of a diene is sequential. In the figure, the crosses are experimental points for mononitrile whereas the squares are experimental points for dinitrile. The lines are theoretical fits resulting from the use of a sequential kinetic model

in the kinetic modeling computer program, GIT (available through the Quantum Chemistry Program Exchange, Department of Chemistry, Indiana University, Bloomington, Ind.). The successful fit illustrates that k$_1$ is 3.5 times greater than $k_2$ and that essentially all dinitrile is derived from mononitrile.

DETAILED DESCRIPTION OF THE INVENTION

The halogen addition reactions of Examples 1–4 and 21, 23, 25, 27, and 28 may be conducted at conditions of time and temperature sufficiently strenuous to result in acceptable conversion of the starting materials, but not strenuous enough to result in low yield of the desired product. The mole ratio of the halogen to the dioxole may be 0.6 to 1.4, preferably 1:1.

The ethylene addition reactions of Examples 5, 7, 8, and 14, may be started at room temperature and heated gradually or rapidly to the final reaction temperature of 200°–250°, preferably 220° as in the Examples. The time at temperature may be 0.5 to 24 hours, depending on the temperature chosen. Longer time is needed at lower temperature.

The dehydrohalogenation reactions of Examples 6, 9, 10 and 15 use a concentrated strong base, preferably KOH or NaOH, at 30°–60° for 10–24 hours. Preferably a quaternary ammonium salt is added to a phase transfer catalyst.

The oxidation of the vinyl compounds to carboxyl compounds, Examples 11, 12 and 18, uses a permanganate salt at 25°–75°, continuing until the exothermic reaction is finished. Inorganic acid or a quaternary ammonium salt is an optional additive.

The polymerizations may be carried out in any of the methods known for polymerization of tetrafluoroethylene, such as aqueous, nonaqueous, and two-phase. The temperature is selected to match the decomposition rate of the initiator chosen, which should be non-telogenic.

The copolymers, which contain at least 1 weight % of the vinyl compound of this invention, are useful for electrical insulation, among other uses. The compounds with five-membered rings are useful as monomers or intermediates to monomers. The product of Example 33 is useful as a polymer catalyst. The product of Example 34 is useful as starting material for the preparation of solvents and stable fluids.

In the following examples, temperatures are in degrees Celsius.

The present invention provides partially fluorinated compounds which are useful as chemical intermediates. The unsaturated nitrile compounds are useful for the preparation of unsaturated acids, amines and esters. The unsaturated nitriles and esters are intermediates for the production of dinitriles and esternitriles of the present invention. The dinitrile compounds are useful as intermediates for the production of diacids, diesters, diisocyanates, and diamines. The esternitrile compounds can be also converted to esteramines. These difunctional species are useful for the synthesis of partially fluorinated condensation polymers. Polymers prepared with compounds of the invention demonstrate improved hydrolytic stability and altered dielectric constants.

Compounds of the invention include compounds of the formula $$H_2C=CH-R_f-CH_2CH_2-Y \quad (1)$$

wherein Y is selected from the group consisting of —CN, —CH$_2$NH$_2$, —COOH, —CH$_2$OH, —CH$_2$N=C=O, —CONH$_2$, —CHO, —COCl, and —COOR, wherein R is $C_nH_{2n+1}$ and n is an integer from 1 to 10, inclusive; and $R_f$ is a fluorinated divalent organic radical selected from the group consisting of linear, branched, carbocyclic, and mixtures thereof having from 1 to about 40 carbon atoms.

Preferably, Y is —CN. In preferred embodiments, $R_f$ is either the branched and carbocyclic 4,5—(2,2-trifluoromethyl)-1,3-dioxolanediyl

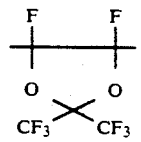

(as shown in Example 14) or of the formula —(CF$_2$CF$_2$)$_n$— wherein n is an integer from 1 to 6.

The invention additionally provides compounds of the formula $$Y'-CH_2CH_2-R_f-CH_2CH_2-Y' \quad (2)$$

wherein Y' is independently selected from the group consisting of —CN, —CN$_2$NH$_2$, —CH$_2$OH, —CH$_2$N=C=O, —CONH$_2$, —CHO, —COCl, and —COOR, wherein R is $C_nH_{2n+1}$; and n is an integer from 1 to 10, inclusive; and $R_f$ is as generally defined above.

Preferably, Y' is —CN. In preferred embodiments, $R_f$ is either the branched and carbocyclic 4,5-trifluoromethyl)-1,3-dioxolanediyl or of the formula —(CF$_2$CF$_2$)$_n$— wherein n is an integer from 1 to 6.

Compound (2) can be employed in a condensation type of polymerization reaction to prepare polymers (A) and (B) of the invention. Polymer (A) results when Y' in compound (2) is —CH$_2$NH$_2$, —CH$_2$OH, —CH$_2$N=C=O, —CONH$_2$, —COCl, or —COOR, wherein R is $C_nH_{2n+1}$ and n is an integer from 1 to 10. Additionally, HOOC—CH$_2$CH$_2$—R$_f$—CH$_2$CH$_2$—COOH can be used to make polymer (A). Polymer (A) can be either polymers comprising 100 mole percent of at least one independently selected repeating unit of the formula $$+X-CH_2CH_2-R_f-CH_2CH_2-X-X'Z-X'+ \quad (3)$$

wherein X is independently selected from the group consisting of NHCH$_2$—, OCH$_2$—, —C(=O), and —CH$_2$NH(C=O); X' is independently selected from the group consisting of NH—, O—, and —C(=O), provided that when X is NHCH$_2$— or OCH$_2$—, X' must be —C(=O), and also provided that when X is —C(=O) or —CH$_2$NH(C=O), X' must be NH— or O—; Z is any divalent organic radical; and $R_f$ is as generally defined above; or copolymers comprising from 1 to 99 mole percent of at least one independently selected repeating unit of formula (3) and from 99 to 1 mole percent of at least one independently selected repeating unit of the formula $$+X''-Z-X''-X'-Z-X'+ \quad (4)$$

wherein X' and Z are as defined above, and Z is independently selected, and X" is independently selected from the same group as X', provided that when X' is —C(=O), X" must be NH— or O—, and also provided that when X' is NH— or O—, X" must be —C(=O). In the nomenclature for polymer (A), the dashes found in the X, X' and X" divalent groups indicate the side of the group that is attached either to —CH$_2$CH$_2$—R-

$R_f$—CH₂CH₂— in repeating unit (3) or to Z in repeating units (3) and (4).

In repeating unit (3), the preferred $R_f$ is either the branched and carbocyclic 4,5-(2,2-trifluoromethyl)-1,3-dioxolanediyl or of the formula —(CF₂CF₂)$_n$— wherein n is an integer from 1 to 6. A preferred Z group in repeating units (3) and (4) is a divalent organic radical independently selected from the group consisting of linear, branched, carbocyclic, aromatic, and mixtures thereof having from 1 to about 20 carbon atoms. Other preferred Z groups are —CH₂CH₂—$R_f$—CH₂CH₂—, provided that the X' or X" attached to —CH₂CH₂—$R_f$—CH₂CH₂— is —C(=O), and —CH₂CH₂CH₂—$R_f$—CH₂CH₂CH₂—, provided that X' or X" attached to —CH₂CH₂CH₂—$R_f$—CH₂CH₂CH₂— is independently selected from the group consisting of —NH and —O, wherein $R_f$ is as generally and specifically defined above. Another preferred Z group is mesogenic divalent organic radicals. Mesogenic divalent organic radicals can include, but are not limited to, divalent radicals of the formula

—V—W—V— wherein V is a divalent radical independently selected from the group consisting of 1,4-phenylene, 4,4'-biphenylene, naphthylidene, 1,4-[2.2.2]-bicyclooctylidene, and 1,4-cyclohexylidene, and W is a divalent radical selected from the group consisting of —CH=N—, —N(O)=N—, —N=N—, —C(=O)—O—, —C=C—, —CH=CH—, —CH=C(CH₃)—, —C(=O)—NH—, —CH=CH—CH=N—, —CH=CH—C(=O)—O—, and —CH=N—N=CH—. The most preferred embodiment of Z is when Z is selected from the group consisting of —C₆H₄—, —C₁₀H₆—, and —(CH₂)$_n$—, wherein n is an integer from 2 to 20.

When Y' is —CH₂NH₂ in compound (2), a condensation type of polymerization reaction can yield polymer (B). Polymer (B) can be either polymers comprising 100 mole percent of at least one independently selected repeating unit of the formula

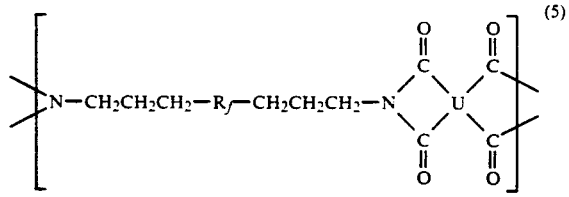 (5)

wherein U is any tetravalent organic radical and $R_f$ is as generally defined above; or copolymers comprising 1 to 99 mole percent of at least one independently selected repeating unit of formula (5) and 99 to 1 mole percent of at least one independently selected repeating unit of the formula

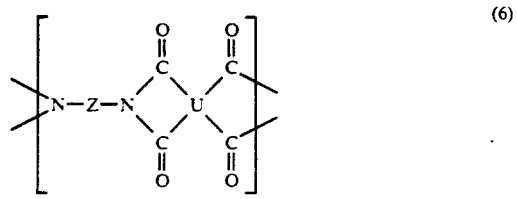 (6)

wherein U and Z are as described above.

In repeating unit (5), the preferred $R_f$ is either the branched and carbocyclic 4,5—(2,2-trifluoromethyl)-1,3-dioxolanediyl or of the formula —(CF₂CF₂)$_n$— wherein n is an integer from 1 to 6. A preferred U group in repeating units (5) and (6) is a divalent organic radical selected from the group consisting of linear, branched, carbocyclic, aromatic, and mixtures thereof having from about 6 to about 20 carbon atoms and containing from 0 to about 5 sulfonyl linkages. Most preferred embodiments of U are 1,2,4,5-benzenetetrayl, 2,2-bis(3,4-phenylene)-propane and 2,2-bis(3,4-phenylene)-1,1,1,3,3,3-hexafluoropropane. In repeating unit (6), a preferred Z group is a divalent organic radical independently selected from the group consisting of linear, branched, carbocyclic, aromatic, and mixtures thereof having from 1 to about 20 carbon atoms. Other preferred embodiments of Z are m-phenylene and p-phenylene.

Compound (1) of the invention wherein Y is —CN can be made by contacting CH₂=CH(R$_f$)$_n$CH=CH₂ with HCN in the presence of a nickel catalyst and a Lewis acid promoter such as zinc chloride by a process similar to that described in U.S. Pat. No. 3,496,217, the disclosure of which is incorporated herein by reference. The diene starting compound can be prepared by the method disclosed in Kim et al., J. Fluor. Chem. 1:203 (1971) or by other conventional chemistry.

Compound (2) of the invention wherein one or both values for Y' is —CN can be made by contacting compound (1) with HCN in a manner similar to that described above. The addition of two equivalents of HCN to the diene to make compound (2), without isolation of the intermediate compound (1), is sequential, i.e., the dinitrile is produced only from the mononitrile. The kinetic analysis shown in FIG. 1 wherein $R_f$ is —CF₂CF₂— illustrates this and shows that compound (2) is produced only from compound (1). Similar analyses have been carried out for many other $R_f$ values and produced the same result.

Other Y values for compounds (1) and (2) result from converting the —CN group to other useful functional groups by conventional chemistry. For example, the —CN group can be converted to the —CH₂NH₂ group by reaction with hydrogen in the presence of ammonia and Raney cobalt. The —CONH₂ group can be prepared by reaction of the —CN group with water in the presence of sulfuric acid. The —COOH group can be prepared by heating the —CN group in 50% sulfuric acid in water. The —COCl group can be made by reacting the —COOH group with a reagent such as thionyl chloride or phosphorus pentachloride. The —COOR group can be made by heating the —CN group in ROH solution in the presence of sulfuric acid. The —CHO group can be made by partially reducing the —COOR group with a reagent such as lithium tri-t-butoxyaluminum hydride. The —CH₂OH group can be made by the reduction of the —COOR, or —COOH group, e.g., by reacting with lithium aluminum hydride. The —CH₂N=C=O group can be prepared by the reaction of the —CH₂NH₂ group with phosgene.

Compound (1) of the invention has utility for the preparation of the difunctional compound (2). Compound (2) of the invention is useful as an intermediate for the synthesis of polymer (A) and polymer (B) of the invention by condensation type polymerization. Partially fluorinated polyamides can be made by heating a salt of the desired acid and amine and allowing the water formed in the reaction to distill off. Higher molecular weights can be obtained by vacuum finishing the molten polymer using standard techniques. Polyesters of the invention can be made by heating a partially fluorinated free acid with the diacetate of a diol using calcium acetate as a catalyst. Polyimides of the invention can be made by adding a dianhydride to a solution of partially fluorinated diamine in a solvent such as dimethylacetamide (DMAC). The resulting amidacid can be cast as a film and imidized by heating in a vacuum.

Methods for conducting condensation type polymerization are well known in the art. For example, 4,4,5,5-tetrafluorosuberic acid can be polymerized with hexamethylenediamine by heating a salt prepared from these materials. Also, 4,4,5,5,6,6,7,7-octofluorosebecic acid can be polymerized with 1,4-butanediol diacetate by heating in the presence of calcium acetate as a catalyst. Most examples of polymer (A) are moldable or melt processible, and most examples of polymer (B) can be processed like other polyimides.

It has been found that incorporation of compound (2) as a monomer improves the thermal characteristics of the resulting polymers (A) and (B). For example, poly(hexamethylenesuberamide) has a melting point of 232° C., whereas poly(hexamethylene-4,4,5,5-tetrafluorosuberamide) has a melting point of 268° C. This increase in melting point is evident also in polyesters. For example, poly(tetramethylenesuberate) melts at 60° C., whereas poly(tetramethylene-4,4,5,5-tetrafluorosuberate) melts at 123° C.

The partially fluorinated compounds of the invention can increase the anisotropic range of polymers in which they are incorporated as a monomer. For example, poly(oxydecanedioyloxy-1,4-phenylene-2-methylvinylene-1,4-phenylene) melts at 210° C. to a nematic anisotropic phase. The resulting melt becomes isotropic at 254° C., with an anistropic range of 44° C. In contrast, poly(oxyoctafluorodecanediooyloxy-1,4-phenylene-2-methylvinylene-1,4-phenylene) melts at 153° C. to a more highly ordered, smectic anisotopic state. The resulting melt becomes isotropic at 280° C., with an anisotropic range of 127° C.

The partially fluorinated compounds of this invention can alter the solubility properties of polymers in which they are incorporated as a monomer. For example, where poly(oxydecanedioyloxy-1,4-phenylene-2-methylvinylene-1,4-phenylene) is soluble in chloroform, poly(oxyoctafluorodecanedioyloxy-1,4-phenylene-2-methylvinylene-1,4-phenylene) is insoluble in all common organic non-acid solvents. The compounds and polymers of the present invention are described in the following examples.

EXAMPLES

Part A

In this part of the Examples section, there is disclosed and taught the preparation of various dioxanes of the invention. Several of these dioxolanes are subsequently employed in the preparation of the partially fluorinated compounds and polymers of the invention which are the subject of the examples of Part B herein.

EXAMPLE 1

Preparation of
Bis-2,2-trifluoromethyl-4,5-difluoro-4,5-diiodo-1,3-dioxolane (I)

A mixture of 54 g. iodine and 52 g. 2,2-bis-trifluoromethyl-4,5-difluorodioxole, (II) was heated in a tube for four hours at 100°. The product was filtered and distilled to give 67.2 g. (I), boiling at 44°-45° at 10 torr. The $^{19}F$ NMR spectrum [trans isomer −26.7 (2F), −79.0 (6F); cis isomer −39.5 (2F), −77.8 (3F), −79.0 (3F)] and the infrared spectrum were consistent with structure (I).

EXAMPLE 2

Preparation of
Bis-2,2-trifluoromethyl-4-bromo-5-iodo-4,5-difluoro-1,3-dioxolane (III)

(II), 98 g., was slowly added to a mixture of 83 g. iodine bromide and 100 ml. 1,1,2-trichloro-1,2,2-trifluoroethane. The reaction mixture was treated with aqueous sodium bisulfite and distilled to give 97.8 g. (III), boiling at 64° at 50 torr. The $^{19}F$ NMR spectrum [trans isomer −32.5 (1F), −33.9 (1F), −79.0 and −79.8 (6F); cis isomer −38.0 (1F), −53.1 (1F), −79.0 and 79.8 (6F)] and the infrared spectrum were consistent with structure (III).

EXAMPLE 3

Preparation of
Bis-2,2-trifluoromethyl-4-chloro-5-iodo-4,5-difluoro-1,3-dioxolane (IV)

A mixture of 49 g. iodine monochloride and 48.8 g. (II) was heated in a tube at 100° for four hours. The product was treated with aqueous sodium bisulfite and distilled to give 49.2 g. (IV) boiling at 50° at 50 torr. The $^{19}F$ NMR spectrum [trans isomer −36.4 (1F), −40.0 (1F), −80.2 (6F); cis isomer −38.3 (1F), −61.7 (1F), −79.5 (3F), −80.2 (3F)] and the infrared spectrum were consistent with structure (IV).

EXAMPLE 4

Preparation of
Bis-2,2-trifluoromethyl-4,4,5-trifluoro-5-iodo-1,3-dioxolane (V)

Iodine pentafluoride, 6.1 g., was added to a mixture of 12.8 g. iodine and 50 ml. 1,1,2-trichloro-1,2,2-trifluoroethane. After stirring 30.5 g. (II) was added, stirred at room temperature for 16 hours and heated to reflux for 2.5 hours. After cooling the reaction mixture was treated with aqueous sodium bisulfite and distilled to give 2.1 g. (V) boiling at 40° at 100 torr. The $^{19}F$ NMR spectrum [−46.7 (1F), −60.4 and −87.3 AB (2F) $J_{AB}=127$ Hz., −80.9 (6F)] was consistent with structure (V).

EXAMPLE 5

Preparation of

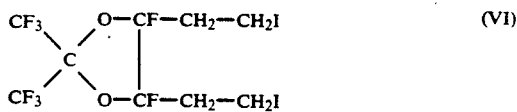

A mixture of 66.0 g. (I) and 15 g. of ethylene was heated at 150° for 30 minutes, 200° for 30 minutes and 220° for 10 hours. The product was distilled to give 47.0 g. (VI) boiling at 105° at 4 torr. The $^{19}F$ NMR spectrum [trans isomer −79.4 (6F), −106.8 (2F); cis isomer −79.4 (3F), −80.5 (3F), −109.0 (2F)], $^1H$ NMR spectrum [3.6 (4H), 2.95 (4H)] and infrared spectrum were consistent with structure (VI).

EXAMPLE 6

Preparation of

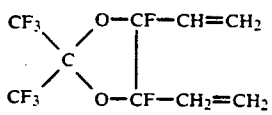

A mixture of 100 ml. 50% aqueous potassium hydroxide, 0.9 g. bis(2-hydroxypropyl)benzyldodecylammonium chloride, (VIII), and 46.2 g. (VI) was heated at 50° for 16 hours. The reaction mixture was distilled and the lower layer redistilled to give 19.1 g. (VII) boiling at 130°. The infrared spectrum, $^{19}F$ NMR spectrum [−79.6 (6F), −108.2 (2F)] and 1H NMR spectrum were consistent with structure (VII).

EXAMPLE 7

Preparation of

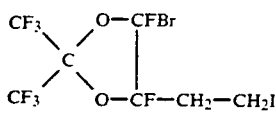

A mixture of 95.0 g. (III) and 10 g. ethylene was heated at 220° for four hours. The product was distilled to give 87.1 g. (IX) boiling at 86° at 20 torr. The infrared and NMR spectra [$^1H$ 3.7 (2H), 3.2 (2H); $^{19}F$ trans isomer −53.0 (1F), −79.4 (3F), −80.0 (3F), −94.5 (1F); cis isomer −55.9 (1F), −79.4 (3F), −80.0 (3F), −105.6 (1F) were consistent with structure (IX).

EXAMPLE 8

Preparation of

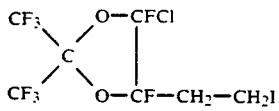

A mixture of 28.5 g. (IV), 51.9 g. 1,1,2-trichloro-1.2.2-trifluoroethane and 10 g. ethylene was heated at 150° for 30 minutes, 200° for 30 minutes and 220° for 10 hours. The product was distilled to give 29.8 g. (X) boiling at 80°-82° at 25 torr. The infrared and NMR spectra [$^1H$ 3.5 (2H), 3.0 (2H); $^{19}F$ trans isomer −59.2 (1F), −80.0 (3F), −80.5 (3F), −99.2 (1F); cis isomer −63.9 (1F), −80.0 (3F), −80.5 (3F), −105.8 (1F)] were consistent with structure (X).

EXAMPLE 9

Preparation of

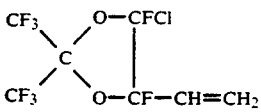

A mixture of 50 ml. 50% aqueous sodium hydroxide, 0.6 g. (VIII), and 29.8 g. (X) was heated at 45°-50° for 16 hours. The reaction mixture was distilled to give 19.1 g. (XI) as a lower layer, b.p. 108°. The $^1H$ [complex peaks 5.2 to 5.7] and $^{19}F$ NMR [trans isomer −57.9 (1F), −81.0 (3F), −81.5 (3F), −102.2 (1F); cis isomer −66.5 (1F), −81.0 (3F), −81.5 (3F), −106.7 (1F)] were consistent with structure (XI).

EXAMPLE 10

Preparation of

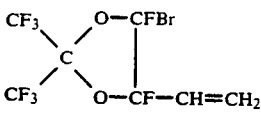

A mixture of 103 ml. 50% aqueous sodium hydroxide, 2.5 ml. of 60% (VIII) and 87.1 g. (IX) was heated at 50° for 16 hours. The mixture was distilled to give a liquid with two layers. The lower layer was redistilled to give 40.7 g. (XII) boiling at 120°-122°. The infrared and NMR spectra [$^1H$ complex peaks 5.5 to 6.1; $^{19}F$ trans isomer −50.8 (1F), −79.7 (3F), −80.3 (3F), −97.1 (1F); cis isomer −57.3 (1F), −79.7 (3F), −80.3 (3F), −105.0 (1F)] were consistent with structure (XII).

EXAMPLE 11

Preparation of

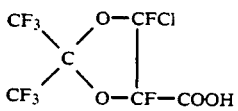

A cooled mixture of 134 ml. water, 27 g. conc. sulfuric acid and 32 g. potassium permanganate was stirred and 16.6 g. (XI) added slowly. The mixture was heated slowly and an exothermic reaction took place at 50°. After cooling the potassium permanganate and manganese dioxide were destroyed by reaction with aqueous sodium sulfite. The lower layer was separated and the upper layer extracted four times with 75 ml. ether. The combined ethereal extracts and lower layer were combined, dried with calcium chloride and distilled to give 7.3 g. (XIII) boiling at 107° at 40 torr. The infrared and NMR spectra [$^1H$ 11.15; $^{19}F$ trans isomer −58.0 (1F), −80.3 (3F), −81.1 (3F), −102.1 (1F); cis isomer −64.2 (1F), −80.3 (3F), −81.1 (3F), −107.8 (1F)] were consistent with structure (XIII).

EXAMPLE 12

Preparation of

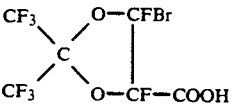

A mixture of 177 ml. water, 74.3 g. potassium permanganate and 3.54 g. methyltrioctylammonium chloride was stirred and 40.7 g. (XII) added in 45 minutes. The temperature rose to 52° and was maintained at 4°-45° with external cooling for 5 hours. After heating to 70° followed by immediate cooling the mixture was allowed to stand at room temperature for 16 hours. After acidification with sulfuric acid the excess potassium permanganate and manganese dioxide were destroyed with aqueous sodium bisulfite. The lower layer was separated and the upper layer extracted twice with 100 ml. ether The extracts were combined with the lower level, dried with anhydrous magnesium sulfate and distilled to give 22.4 g. (XIV) boiling at 99° at 20 torr. The $^{19}$F NMR spectrum [trans isomer −53.8 (1F), −80.5 (6F), −98.0 (1F); cis isomer −58.5 (1F), −79.7 (3F), −80.5 (3F), −107.7 (1F)] was consistent with structure (XIV).

EXAMPLE 13

Preparation of

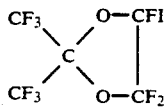 (XV)

A mixture of 48.8 g.(II), 45 g. yellow mercuric oxide, 127 g. iodine, 12 g. anhydrous hydrogen fluoride, 0.1 g. phenothiazine and 0.055 g. hydroquinone was heated in a stainless steel tube at 50° for two hours, the temperature raised to 125° over a two hour period and at 125° for three hours. The reaction mixture was poured into ice water and the lower organic layer distilled to give 50.0 g., 64%, (XV) boiling at 74°-76°. The $^{19}$F NMR spectrum was consistent with structure (XV).

EXAMPLE 14

Preparation of

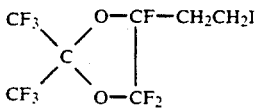 (XVI)

A mixture of 11.7 g. (XV) and 5.0 g. ethylene was heated in a stainless steel tube at 220° for 10 hours. The liquid product was distilled to give 7.0 g., 56%, (XVI) boiling at 95° at 100 torr. The NMR spectra [$^1$H 2 90 (2H), 3.43 (2H); $^{19}$F −77.8 (1F), −80.9 (3F), −81.6 (3F), −88.3 (1F), −110.0 (1F)] are consistent with structure (XVI).

EXAMPLE 15

Preparation of

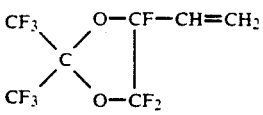 (XVII)

A mixture of 16.7 g. (XVI), 20 ml. 10M potassium hydroxide and 0.86 g. (VIII) was stirred at room temperature and monitored by gas chromatography until no more (XVI) remained. The lower organic layer was separated, washed with water, dilute hydrochloric acid and distilled to give 9.5 g., 82%, (XVII) boiling at 70°-72°. The NMR spectra [$^1$H 5.40-5.90 complex; $^{19}$F −75.7 (1F), −82.0 (3F), −82.6 (3F), −90.3 (1F), −112.8 (1F)] are consistent with structure (XVII).

EXAMPLE 16

Copolymerization of (XVII) and Tetrafluoroethylene

A mixture of 5.0 g. (XVII), 30 g. of 1,1,2-trichloro-1,2,2-trifluorethane, 0.05 g. "Percadox" 16N, 1.0 g. tetrafluoroethylene and 750 psi nitrogen was heated at 60° for 5 hours. The solvent was evaporated to yield 0.5 g. polymer containing 84.1 mole percent tetrafluoroethylene and 15.9 mole percent (XVII) as determined by $^{19}$F NMR spectroscopy.

EXAMPLE 17

Preparation of

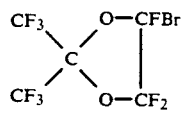 (XVIII)

A mixture of 97.6 g. (II), 90 g. yellow mercuric oxide, 160 g. bromine, 36 g. anhydrous hydrogen fluoride, 0.2 g. phenothiazine and 0.11 g. hydroquinone was heated at 50° for two hours, the temperature raised to 120° over a two hour period and held at 120° for three hours. After filtration and washing with a saturated solution of sodium thiosulfate the organic layer was distilled to give 13.5 g., (10%), (XVIII) boiling at 60° and 66 g., (41%), bis-2,2-trifluoromethyl4,5-dibromo-4,5-difluoro-1,3-dioxolane. The $^{19}$F NMR spectrum [−54.5 (1F), −67.1 (1F), −81.6 (6F), −85.6 (1F)] is consistent with structure (XVIII).

EXAMPLE 18

Preparation of

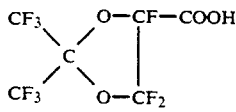 (XIX)

(XVII), 29.0 g, was slowly added to a mixture of 50 g. concentrated sulfuric acid, 100 ml. water and 31.6 g. potassium permanganate. After stirring for 6 hours at room temperature the reaction mixture was extracted with ether, the organic layer washed with water and distilled to give 8.0 g., 26%, (XIX), boiling at 71°-71° [?] at 12-15 Torr. The $^{19}$F NMR spectrum [−74.8 (1F), −80.6 (6F), −84.5 (1F), −113.7 (1F)] is consistent with structure (XIX).

EXAMPLE 19

Preparation of

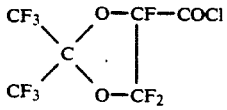 (XX)

Thionyl chloride, 14.3 g., was slowly added to a mixture of 30 g. (XIX) and 3.16 g. pyridine and slowly heated to 85°-90°. After heating at this temperature for 1.5 hours the volatile product was codistilled with thionyl chloride and was separated in a separatory funnel. (XX), 15.0 g., boiled at 79°-80°. The $^{19}$F NMR spectrum [−74.5 (1F), −81.3 (3F), −81.8 (3F), −84.0 (1F), −109.1 (1F)] is consistent with structure (XX).

EXAMPLE 20

Preparation of

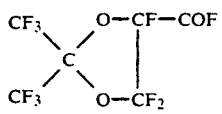 (XXI)

A mixture of 6.53 g. (XX), 4.06 g. potassium fluoride and 10 ml. tetramethylene sulfone was slowly heated to 140°. (XXI), 4.5 g., 72.6%, was obtained as a clear colorless oil boiling at approximately 50°. The $^{19}F$ NMR spectrum [+23.9 (1F), −74.4 (1F), −81.2 (6F), −84.1 (1F), −113.3 (1F)] is consistent with structure (XXI).

EXAMPLE 21

Preparation of

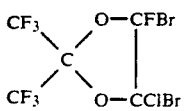 (XXII)

Bromine was slowly added to 17.7 g. of 2,2-bistrifluoromethyl-4-chloro-5-fluoro-1,3-dioxole under irradiation with a sun lamp. The excess bromine was destroyed with aqueous sodium bisulfite and the lower organic layer washed with water and distilled to give 16.8 g. (XXII) boiling at 85° at 100 torr. The infrared and $^{19}F$ NMR spectra [−28.5 (0.63F) trans, −34.8 (0.37F) cis, −77.8 to −80.0 (6F)] are consistent with a mixture of cis and trans isomers of (XXII).

EXAMPLE 22

Preparation of

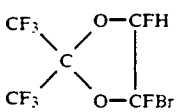 (XXIII)

A mixture of 300 ml. isopropanol and 121.5 g. 2,2-bistrifluoromethyl-4,5-dibromo-4,5-difluoro-1,3-dioxolane was irradiated with a sun lamp for 25 hours. The portion of the reaction mixture boiling from 52°-80° was washed with water and distilled to give 50.0 g. of the cis and trans isomers of (XXIII) boiling at 90°. The infrared and NMR spectra [$^1H$ 6.06 (trans), 6.36 (cis); $^{19}F$ trans isomer −53.5 (1F), −80.7 (6F), −113.8 (1F), cis isomer −63.3 (1F), −80.7 (6F), −122.5 (1F)] are consistent with cis and trans isomers of structure (XXIII).

EXAMPLE 23

Preparation of

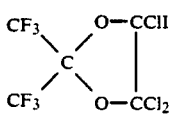 (XXIV)

A mixture of 27.7 g. 2,2-bis-trifluoromethyl-4,5-dichloro-1,3-dioxole and 18 g. iodine monochloride was irradiated with a sun lamp. The reaction mixture was washed with aqueous sodium bisulfite and the organic layer distilled to give 6.5 g. (XXIV) boiling at 61°-64° at 10 torr. which slowly turned purple on standing. The infrared and $^{19}F$ NMR spectra [−76.4 complex] are consistent with structure (XXIV).

EXAMPLE 24

Preparation of 2,2-Bis-trifluoromethyl-4-chloro-1,3-dioxole (XXV)

A mixture 22.9 g. zinc dust and 120 ml. 2,2-ethoxyethoxyethanol was stirred and 8 ml. 2,2-bis-trifluoromethyl-4,4,5-trichloro-1,3-dioxolane, (XXVI), added. After stirring at room temperature the reaction mixture was heated to 55° and the remainder of (XXVI) was added slowly for a total of 58.8 g. The mixture was stirred for 20 hours and then distilled. The distillate was washed twice with water to give 36.3 g. (XXV) boiling at 75° whose infrared and $^{19}F$ NMR spectra were consistent with structure (XXV).

EXAMPLE 25

Preparation of

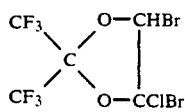 (XXVII)

Bromine was slowly added to 36.3 g. (XXV) while irradiating with a sun lamp. The excess bromine was destroyed with aqueous sodium bisulfite and the organic layer was washed with water and distilled to give 51.9 g. (XXVII) boiling at 63° at 20 torr. The infrared and NMR [$^1H$ 7.24 (trans), 6.98 (cis); $^{19}F$ −77.7, −78.6] spectra are consistent with the cis and trans isomers of structure (XXVII).

EXAMPLE 26

Preparation of

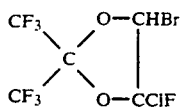 (XXVIII)

A mixture of 51.9 g. (XXVII), 4.0 g. antimony pentachloride and 25 g. anhydrous hydrogen fluoride was heated at 70° for one hour and 100° for three hours and added to a mixture of ice and water. The lower layer was separated and distilled to give 15.7 g. (XXVIII) boiling at 118°. The infrared, mass and NMR [$^1H$ 6.85; $^{19}F$ −47.2 (1F), −78.9 (3F), −80.6 (3F)] spectra are consistent with structure (XXVIII).

EXAMPLE 27

Preparation of

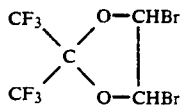 and 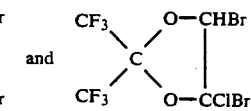

(XXIX)          (XXX)

A 15.6 g. mixture of 2,2-bis-trifluoromethyl-1,3-dioxole and 2,2-bis-trifluoromethyl-4-chloro-1,3-dioxole was irradiated with a sun lamp. Bromine was added slowly and after 25 minutes the excess bromine was destroyed with aqueous sodium bisulfite. The organic layer was washed with water, dried with calcium chloride and distilled to give (XXIX) boiling at 69° at 50 torr and (XXX) boiling at 78° at 50 torr. The NMR spectra were consistent with these structures. [(XXIX) $^1$H 7.02; $^{19}$F −77.7; (XXX) $^1$H 7.29; $^{19}$F −77.6 (3F) −78.4 (3F)]

EXAMPLE 28

Preparation of $$\text{CF}_3 \diagdown \text{C} \diagup \text{O—CClBr} \atop \text{CF}_3 \diagup \text{ } \diagdown \text{O—CClBr} \qquad \text{(XXXI)}$$

The procedure of Example 27 was followed and 65.0 g. 2,2-bis-trifluoromethyl-4,5-dichloro-1,3-dioxole was brominated to give 93.9 g. cis/trans (XXXI) boiling at 97° at 50 torr. The infrared and NMR spectra [$^{19}$F trans −76.5, cis −76.1 (3F), −76.8 (3F)] are consistent with structure (XXXI).

EXAMPLE 29

Preparation of $$\text{CF}_3 \diagdown \text{C} \diagup \text{O—CH}_2 \atop \text{CF}_3 \diagup \text{ } \diagdown \text{O—CFH} \qquad \text{CF}_3 \diagdown \text{C} \diagup \text{O—CF}_2 \atop \text{CF}_3 \diagup \text{ } \diagdown \text{O—CClH}$$

(XXXII)          (XXXIII)

A mixture of 43.8 g. 2,2-bis-trifluoromethyl-4,4,5-trichloro-1,3-dioxolane, 5.0 g. antimony pentachloride and 25 g. anhydrous hydrogen fluoride was heated at 70° for one hour and 120° for five hours. The reaction mixture was poured into ice and water. The lower layer was separated and distilled to give 13.4 g. (XXXII) boiling at 54° and 11.7 g. (XXXIII) boiling at 75°. The NMR and infrared spectra were consistent with structures (XXXII) and (XXXIII). [NMR (XXXII) $^1$H 5.68; $^{19}$F −77.6 (1F), −82.6 (3F), −83.2 (3F), −90.2 (1F), −130.9 (1F); (XXXIII) $^1$H 6.18; $^{19}$F −73.3 (1F), −78.0 (1F), −81.1 (3F), −82.3 (3F)]

EXAMPLE 30

Preparation of $$\text{CF}_3 \diagdown \text{C} \diagup \text{O—CF}_2 \atop \text{CF}_3 \diagup \text{ } \diagdown \text{O—CCl}_2 \qquad \text{(XXXIV)}$$

A glass ampoule containing 8.8 g. (XXXIII) and 8.4 g. chlorine was sealed and irradiated with a sun lamp for 16 hours. The tube was opened, washed with aqueous sodium bisulfite, water and distilled to give 4.7 g. (XXXIV) boiling at 86°. The infrared and NMR [$^{19}$F −71.1 (2F), −80.8 (6F)] spectra were consistent with structure (XXXIV).

EXAMPLE 31

Copolymerization of Tetrafluoroethylene and (VII)

A mixture of 12.1 g. (VII). 0.2 g. bis(4-t-butylcyclohexyl) peroxydicarbonate, (XXXV), 45 g. tetrafluoroethylene and 100 ml. 1,1,2-trichloro-1,2,2-trifluoroethane was heated at 60° for one hour. 70° for one hour and 80° for one hour. The reaction mixture was evaporated to give a solid residue which was washed with an acetone/water mixture and then acetone. It was dried to yield 7.3 g. of a white solid whose infrared spectrum was consistent with a copolymer of (VII) and tetrafluoroethylene.

EXAMPLE 32

Copolymerization of Tetrafluoroethylene and (XI)

A mixture of 200 ml. of water, 1.0 g. ammonium perfluorononanoate, 0.2 g. ammonium persulfate, 10 g. (XI) and 45 g. tetrafluoroethylene was heated at 80° for one hour and 90° for two hours. The reaction mixture, which contained a liquid and solid, was stirred vigorously with a few drops of triethylenetetramine to give additional copolymer and filtered.

EXAMPLE 33

Preparation of $$[(CH_3)_2N]_3S^+ \text{ }^-\text{O—CF—CF}_2 \atop \text{ } \hspace{2em} \text{CF}_3\text{—C——O} \atop \text{ } \hspace{3em} \text{CF}_3 \qquad \text{(XXXVI)}$$

A mixture of 1.22 g. (II), 10 ml. tetrahydrofuran, and 1.38 g. tris(dimethylamino)sulfonium difluorotrimethyl silicate, (XXXVII), was stirred at −70° and allowed to warm to room temperature. The volatiles were removed to give 1.96 g. residue which was recrystallized to give 1.45 g. (XXXVI) melting at 99°-104°. The $^{19}$F NMR spectrum [−45.6 (1F), −69 (3F), −71.3 (3F), −73.1 (1F), −77.3 (1F)] is consistent with structure (XXXVI).

EXAMPLE 34

Preparation of $$\text{CF}_2\text{—C=O} \atop \text{ } \hspace{0.2em} | \hspace{1em} | \atop \text{O——C—CF}_3 \atop \text{ } \hspace{2em} \text{CF}_3 \qquad \text{(XXXVIII)}$$

A mixture of 3.18 g. (XXXVI) and 15 ml. ether was cooled to 0° and 1.06 g. of boron trifluoride etherate was added. The reaction mixture was heated to 35° and (XXXVIII) removed from the cooled receiver. The infrared [—C=O at 1875 cm.−1] and $^{19}$F NMR spectra [−69.67 (2F), −72.83 (6F)] were consistent with structure (XXXVIII). The solid residue from the reaction mixture was recrystallized from acetonitrile to give 1.63 g. (87%) tris(dimethylamino)sulfonium tetrafluoroborate.

Part B

In the Examples, compounds (1) and (2) were prepared according to the following general procedure. A 3-necked, round-bottom flask equipped with an overhead mechanical stirrer, reflux condenser (used with a low temperature circulation bath), nitrogen bubbler, and rubber septum was charged under nitrogen with the specified catalyst components, toluene, and the desired diene. The resulting mixture was heated in a 50° C. oil bath. Hydrogen cyanide was fed to the mixture by vapor transfer by passing nitrogen gas through liquid hydrogen cyanide cooled to 0° C. in an ice bath. Under these conditions, the saturated vapor mixture was approximately 30-40% hydrogen cyanide. The hydrogen cyanide vapor was admitted to the reaction vessel via a syringe needle passed through the rubber septum and placed slightly above the liquid level. The vapor absorbed into the reaction mixture. The reflux condenser was cooled to −14° C. to prevent escape of nonabsorbed hydrogen cyanide. Progress of reactions was monitored by removing samples with a syringe, diluting with acetone, and analyzing by capillary gas chromatography (cross-linked methyl silicone column, 25 m, 0.2 mm inner diameter).

EXAMPLE 35

Preparation of $H_2C=CH-(CF_2)_2-CH_2CH_2-CN$ and $NC-CH_2CH_2-(CF_2)_2-CH_2CH_2-CN$ A reaction mixture comprised of Ni(p-TTP)$_4$ (0.30 g; 0.20 mmol), p-TTP (0.25 mL; 0.82 mmol) (wherein p-TTP is tri-p-tolylphosphite), toluene (8.0 mL), BPh$_3$ (0.05 g; 0.2 mmol), and $CH_2=CH(CF_2)_2CH=CH_2$ (2.24 g; 0.45 mmol) was treated at 50° C. with hydrogen cyanide (nitrogen flow=4 mL/min) as described in the general procedure above. Two new peaks which grew with time were observed by capillary gas chromatography (CGC). White solid began to form in the reaction mixture after 1.5 hours. The reaction was stopped, and the white solid was found to be associated with the longer retention time new peak. Subsequent analysis revealed that the new Peaks were associated with $H_2C=CH-(CF_2)_2-CH_2CH_2-CN$ and $NC-CH_2CH_2-(CF_2)_2-CH_2CH_2-CN$ (the white solid).

EXAMPLE 36

Preparation of $H_2C=CH-(CF_2)_2-CH_2CH_2-CN$ and $NC-CH_2CH_2-(CF_2)_2-CH_2CH_2-CN$ A reaction mixture comprised of Ni(TTP)$_4$ (7.0 mL, 5.6 mmol) (wherein TTP is tri-m,p-tolylphosphite), p-TTP (5.0 mL; 16.3 mmol), toluene (125 mL), ZnCl$_2$ (0.50 g; 3.7 mmol) and a mixture of $CH_2=CH(CF_2)_2CH=CH_2$ and acetonitrile (55 g; 80:20) was treated at 50° C. with hydrogen cyanide (nitrogen flow=17 mL/min for 7.5 hours and then 7 mL/min until complete). The reaction mixture was cooled, resulting in precipitation of a white solid. The mixture was filtered to remove the crude dinitrile. The solvent was then removed from the filtrate in vacuo causing more dinitrile to precipitate. The dinitrile was filtered and washed with diethylether. The precipitates were combined and recrystallized from methanol, yielding 25.4 g (34%) of white crystals, m.p. 109°-110° C. Fluorine NMR −116.7, m. Proton NMR 2-2.7, c. IR 2950 cm$^{-1}$, w, (C—H); 2260 cm$^{-1}$, m, (C≡N); 1180 cm$^{-1}$, s, (C≡F). The ether was removed from the filtrate in vacuo and the resulting oil distilled. $H_2C=CHC-(CF_2)_2-CH_2CH_2-CN$ was collected, b.p. 60° C. at 5 mm Hg, 37 g (57%). Proton NMR 6.7-7.2, c, (olefin); 5.6-6.2, c, (olefin); 2.1-2.8, c, (alkyl). Fluorine NMR −115.4, c, 2F; −116.75, c, 2F. IR (neat) 3005 cm$^{-1}$, w, (C—H olefin); 2970 cm$^{-1}$, w, (C—H alkyl); 2226 cm$^{-1}$, m, (C≡N); 1655, m, (C=C); 1110 cm$^{-1}$, vs, (C—F). Elemental Analysis for $NC-CH_2CH_2-(CF_2)_2-CH_2CH_2-CN$:

Calculated: %C 46.16; %H 3.87; %F 36.51;
Found: %C 45.90; %H 4.05; %F 36.22.

EXAMPLE 37

Preparation of $NC-CH_2CH_2-(CF_2)_4-CH_2CH_2-CN$

A reaction mixture comprised of Ni(TTP)$_4$ (15.0 mL, 12.2 mmol), p-TTP (10 mL; 32.6 mmol), toluene (250 mL), acetonitrile (20 mL), ZnCl$_2$ (1.0 g; 7.4 mmol), and $CH_2=CH(CF_2)_4CH=CH_2$ (161.5 g; 636 mmol) was treated at 50° C. with hydrogen cyanide (nitrogen flow=40 mL/min for 1 hour, 32 mL/min for 25 hours, and 16 mL/min for 3 hours). The reaction mixture was cooled to −30° C. for about 18 hours and crude $NC-CH_2CH_2-(CF_2)_4-CH_2CH_2-CN$ was isolated by filtration. The solvent was removed from the resulting filtrate in vacuo resulting in more white solid. The solids were redissolved in acetone and precipitated by addition of pentane. The solid was isolated by filtration and recrystallized from methanol producing white crystals (168 g; 86% yield) m.p. 66°-68° C. Fluorine NMR −116.0, c, 2F; −124.0, dd, 2F.

Elemental Analysis for $NC-CH_2CH_2-(CF_2)_4-CH_2CH_2-CN$:

Calculated %C 38.97; %H 2.62; %F 49.32;
Found: %C 38.73; %H 2.75; %F 49.05.

EXAMPLE 38

Preparation of $NC-CH_2CH_2-(CF_2)_6-CH_2CH_2-CN$

A reaction mixture comprised of Ni(p-TTP)$_4$ (1.0 g; 0.68 mmol), p-TTP (0.75 mL; 2.4 mmol), toluene (15 mL), BPh$_3$ (0.10 g; 0.41 mmol), and $CH_2=CH(CF_2)_6CH=CH_2$ (9.0 mL; 13.3 g; 37.5 mmol) was treated at 50° C. with hydrogen cyanide (nitrogen flow=4 mL/min for 4 hours, 3.5 mL/min for 4 hours, and 2 mL/min for about 18 hours). The entire reaction mixture was redissolved in acetone filtered to remove the nickel containing compounds. Hexanes were added to precipitate the product. The product was filtered and the solids recrystallized from methanol to give white crystals of $NC-CH_2CH_2-(CF_2)_6-CH_2CH_2-CN$ (6.8 g) m.p. 80°-81° C. Proton NMR 2-2.8, c. Fluorine NMR −115.8, m, 2F; −122.3, m, 2F; −124.0, m, 2F.

Elemental Analysis for $NC-CH_2CH_2-(CF_2)_6-CH_2CH_2-CN$:

Calculated: %C 33.09; %H 1.59; %F 59.81;
Found: %C 32.91; %H 1.58; %F 59.46.

EXAMPLE 39

Preparation of $NC-CH_2CH_2-(CF_2)_8-CH_2CH_2-CN$

A reaction mixture comprised of Ni(TTP)$_4$ (7.0 mL, 5.6 mmol), p-TTP (5.0 mL; 16.3 mmol), toluene (130 mL), acetonitrile (10 mL), ZnCl$_2$ (0.50 g; 3.7 mmol), and $CH_2=CH(CF_2)_8CH=CH_2$ (50 g, 110 mmol) was treated at 50° C. with hydrogen cyanide (nitrogen flow=18 mL/min for 3 hours and 13 mL/min for 5 hours). The mixture was diluted with hexanes and cooled to −30° C. to crystallize the $NC-CH_2CH_2-(CF_2)_8-CH_2CH_2-CN$. The crude product was dissolved in acetone and filtered through Celite to remove the spent catalyst. The acetone was then removed, and the product was recrystallized from methanol. The yield was 46 g (82%).

EXAMPLE 40

Preparation of
NC—CH$_2$CH$_2$—(CF$_2$)$_8$—CH$_2$CH$_2$—CN

A reaction mixture comprised of Ni(TTP)$_4$ (20 mL, 16.3 mmol), p-TTP (10 mL; 32.6 mmol) toluene (300 mL), acetonitrile (10 mL), ZnCl$_2$ (1.0 g; 7.4 mmol), and CH$_2$=CH(CF$_2$)$_8$CH=CH$_2$ (200 g; 440 mmol) was treated at 50° C. with hydrogen cyanide (nitrogen flow=35 mL/min) for 26 hours. The mixture was diluted with hexanes and cooled to −30° C. to crystallize NC—CH$_2$CH$_2$—(CF$_2$)$_8$—CH$_2$CH$_2$—CN. The crude product was dissolved in acetone and filtered through Celite to remove the spent catalyst. The acetone was then removed, and the product was then recrystallized from methanol. The yield was 202 g (90%).

EXAMPLE 41

Preparation of
HOOC—CH$_2$CH$_2$—(CF$_2$)$_2$—CH$_2$CH$_2$—COOH

NC—CH$_2$CH$_2$—(CF$_2$)$_2$—CH$_2$CH$_2$—CN (1.0 g) was added to a solution of 50 mL water and 50 mL of concentrated sulfuric acid. The resulting mixture was heated to 130° C. for 18 hours. Upon cooling to 0° C., white crystals formed. The crystals were filtered, washed with cold water, and recrystallized from water. Yield 0.8 g white crystals, m.p. 204°-206° C. Proton NMR (acetone) 2.6, c. Fluorine NMR −115.8, dt. IR (KBr) 3500-2500 cm$^{-1}$, br, (O—H), 1715 cm$^{-1}$, s, (C=O); 1200 cm$^{-1}$, vs, (C—F).

EXAMPLE 42

Preparation of
HOOC—CH$_2$CH$_2$—(CF$_2$)$_4$—CH$_2$CH$_2$—COOH

NC—CH$_2$CH$_2$—(CF$_2$)$_4$—CH$_2$CH$_2$—CN (100 g) was added to 500 mL of water. Concentrated sulfuric acid (700 mL) was slowly added, and the resulting reaction mixture was heated to 150° C. for about 18 hours. Upon cooling to 0° C., crystals formed. The crystals were filtered, washed with water, and recrystallized from water with a hot filtration through Celite. Yield 55 g of white crystals. IR 3500-2400 cm$^{-1}$, br; 1710 cm$^{-1}$, s; 1250-1150 cm$^{-1}$, s..

EXAMPLE 43

Preparation of
H$_3$COOC—CH$_2$CH$_2$—(CF$_2$)$_2$—CH$_2$CH$_2$—COOCH$_3$

HOOC—CH$_2$CH$_2$—(CF$_2$)$_2$—CH$_2$CH$_2$—COOH (25 g) was dissolved in 100 mL methanol. Concentrated sulfuric acid (10 mL) was added, and the resulting solution was refluxed for 4 hours, and then stirred at ambient temperature for 2 days. The solution was cooled to 0° C. and crystals formed. The crystals were filtered, washed with cold methanol, and recrystallized from methanol. The resulting filtrate was added to 500 mL of water and extracted with 4 100 mL portions of ether. The ether layers were washed with 100 mL water, 2 100 mL portions of 10% Na$_2$CO$_3$, 2 100 mL portions of water, and 100 mL of brine. The resulting solution was dried over MgSO$_4$ and then stripped to give white crystals that were recrystallized from methanol. Yield 23 g white crystals, m.p. 64°-66° C. IR (KBr) 1740 cm$^{-1}$, s, (C=O).

EXAMPLE 44

Preparation of
H$_3$COOC—CH$_2$CH$_2$—(CF$_2$)$_2$—CH$_2$CH$_2$—COOCH$_3$

NC—CH$_2$CH$_2$—(CF$_2$)$_2$—CH$_2$CH$_2$—CN (50 g) was dissolved in 200 mL of methanol. Concentrated sulfuric acid (150 mL) was added slowly and the resulting solution was refluxed for 6 hours. The solution was then dumped into 1 L of ice. The resulting mixture was extracted with 3 200 mL portions of ether. The ether layers were washed with 2 100 mL portions of water and 50 mL of brine. The solution was dried over MgSO$_4$ and then stripped to give white crystals which were recrystallized from methanol. Yield 57 g (87%), m.p. 64°-65° C. IR (KBr) 2980 cm$^{-1}$, m; 1740 cm$^{-1}$, s; 1200 cm$^{-1}$, s.

EXAMPLE 45

Preparation of
NC—CH$_2$CH$_2$—(CF$_2$)$_6$—CH$_2$CH$_2$—CN

The method described in Example 40 was substantially repeated except that CH$_2$=CH(CF$_2$)$_6$CH=CH$_2$ (200 g; 565 mmol) was hydrocyanated and NC—CH$_2$CH$_2$—(CF$_2$)$_6$—CH$_2$CH$_2$—CN was produced. Yield 215 g (93%).

EXAMPLE 46

Preparation of
H$_2$N—CH$_2$CH$_2$CH$_2$—(CF$_2$)$_2$—CH$_2$CH$_2$CH$_2$—NH$_2$

NC—CH$_2$CH$_2$—(CF$_2$)$_2$—CH$_2$CH$_2$—CN (4.8 g) was dissolved in 200 mL of THF. This solution was placed in a 400 mL bomb. The bomb was cooled and evacuated. Ammonia (50 g) was added to the bomb and then hydrogen was added until the pressure was 1500 psi at ambient temperature. The bomb was sealed and heated to 110° C. for 10 hours. The bomb was cooled, and the gasses were bled off. The resulting solution was filtered through Celite and then stripped to a pale yellow oil. The oil was dissolved in 300 mL of ether, and HCl gas was bubbled through the resulting solution. A white precipitate formed that was filtered, washed with ether, and dried. The precipitate was recrystallized from a mixture of methanol and ethanol to give 5 g of white crystals. Fluorine NMR (D$_2$O) −114.5, t. Proton NMR 3.0, t, 2H; 2.0, c, 4H.

EXAMPLE 47

Preparation of
H$_2$N—CH$_2$CH$_2$CH$_2$—(CF$_2$)$_8$—CH$_2$CH$_2$CH$_2$—NH$_2$

NC—CH$_2$CH$_2$—(CF$_2$)$_8$—CH$_2$CH$_2$—CN (50 g) was placed into a 400 mL bomb, along with 200 mL of THF and approximately 5 g of Raney cobalt. The bomb was sealed and 50 g of ammonia were added. Hydrogen was added to a pressure of 500 psi at ambient temperature. The bomb was heated to 110° C. and the hydrogen pressure was adjusted to 1500 psi. The temperature and hydrogen pressure were held constant for 18 hours. The bomb was cooled, and the gasses were bled off. The solution was filtered through Celite, and the solvent was removed to give 13 g of a white waxy solid. Proton NMR (CDCl$_3$/F11) 2.7, t, 38; 1.5-2.5, c, 87; 1.0, s, 42. Fluorine NMR −114.6, 2F, −122.3, 4F; −124.0, 2F. IR (KBr) 3400 cm$^{-1}$, m; 3300 cm$^{-1}$, m; 3200 cm$^{-1}$, m; 2960 cm$^{-1}$, m; 1200 cm$^{-1}$, vs.

EXAMPLE 48

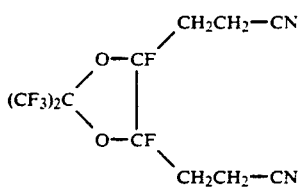

A reaction mixture comprised of Ni(p-TTP)$_4$ (0.25 g; 0.17 mmol), p-TTP (0.5 mL; 1.6 mmol), toluene (5 mL), acetonitrile (0.2 mL), ZnCl$_2$ (0.005 g; 0.038 mmol), and

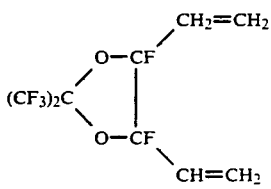

(1.0 g, 3.35 mmol) as treated at 50° C. with hydrogen cyanide (nitrogen flow=3 mL/min) for 20 hours. The resulting reaction mixture was cooled and filtered through Celite. Gas chromatography analysis showed two new products. High resolution GC/MS showed that the first product was

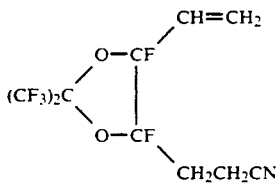

and the second product was

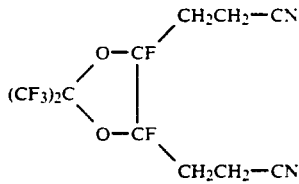

IR (reaction mixture) 2280 cm$^{-1}$, m; 2255 cm$^{-1}$, m; 1300–1100 cm$^{-1}$, vs.

EXAMPLE 49

Preparation of Partially Fluorinated Polyamide Polymer (A)

A 500 mL round-bottom flask was equipped with an overhead stirrer, a nitrogen inlet, and a Liebig's condensor topped with a still head. The flash was charged with 35 g of crystals of the salt of tetrafluorosuberic acid and hexamethylenediamine prepared according to the following procedure. Tetrafluorosuberic acid (25.00 g) was dissolved in 250 mL of hot ethanol, and 11.79 g of hexamethylenediamine were dissolved in 100 mL of hot ethanol. The resulting solutions were combined to produce a suspension containing white crystals. The suspension was stirred for 10 minutes, cooled to 0° C., filtered, washed with ethanol, and dried in vacuo to give 35.97 g of white crystals. This material was immediately immediately charged to the flask as described above.

The flask was heated to 220° C., and the water formed was allowed to reflux. Over a period of about 1 hour, the temperature of the flask was raised to 290° C. The water in the condensor was drained. The water formed in the reaction was allowed to distill off. Over the next hour the temperature of the flask was slowly raised to 300° C., giving a viscous amber melt. The melt was allowed to cool, giving 30 g of an amber polymer.

The inherent viscosity of the polymer in a formic acid solution was 1.07 dl/g. The polymer formed strong melt pressed films which had an aqueous contact angle of 74°. The polymer was also spun to form strong fibers. The melting point of the polymer was 268° C., as compared to 232° C. for the melting point of the nonfluorinated polymer.

EXAMPLE 50

Preparation of Partially Fluorinated Polyester Polymer (A)

A small polymer tube with a side arm was charged with 5.00 g of dimethyltetrafluorosuberate, 1.81 g of butanediol, 3 mg of calcium acetate, and 1.5 mg of antimony oxide. The resuting mixture was degassed and heated to 200° C. A needle with a slow flow of nitrogen was put at the bottom of the melt and the temperature was raised to 275° C. over a period of 3 hours and held there for 16 hours. During this time, first methanol and then butanediol slowly distilled from the resulting melt. The pressure was then reduced to about 1 mm Hg for a period of 30 minutes. The melt was cooled to form an opaque white solid polymer. Fibers and melt pressed films could be made from the polymer. The inherent viscosity of the melt in a chloroform solution was 0.28 dl/g.

The polymer had a melting point of 123° C. as compared to 60° C. for nonfluorinated polymer.

EXAMPLE 51

Preparation of Partially Fluorinated Polyimide Polymer (B)

Dodecafluoro-1,12-dodecadiamine (8.975 g) was dissolved in about 100 mL of N-methylpyrrolidone (NMP) in a 500 mL 3-necked flask equipped with an overhead stirrer and a nitrogen inlet. Pyromelliticdianhydride (4.567 g) was added in several batches, producing a viscous solution containing some gel. About 100 mL of NMP were added to dissolve some of the gel. The resulting solution was filtered through a 0.2 micron filter and cast on a glass plate. The solvent was evaporated at 75° C. for about 18 hours. The polymer was imidized by heating in vacuo at 150° C. for about 16 hours and then at 175° C. for 4 hours to give a tough clear film. The polymer had a melting point of 341° C. and did not decompose below 450° C.

EXAMPLE 52

Preparation of Partially Fluorinated Liquid Crystalline Polyester Polymer (A)

Alpha-methylstilbenediol diacetate (2.62 g), hexadecafluorododecane-1,12-dicarboxylate (5.0 g), and 0.01 g sodium acetate were added to a polymer tube with a side arm. The resulting mixture was melted in a metal bath at 200° C., and a needle with a slow purge of nitrogen was placed at the bottom of the resulting melt. The melt was held at 200° C. for 18 hours while acetic acid distilled off. The temperature was then raised to 250° C. for 5 hours. The nitrogen purge was stopped, and the pressure was reduced to about 1 mm Hg for 1 hour. The resulting combination was cooled to give an off-white solid polymer. The polymer melted at 230° C. to a smectic anisotropic state. The resulting melt remained anisotropic until a temperature of 310° C. was reached, at which point the melt was isotropic. Upon cooling, the smectic state returned at about 270° C., and remained anisotropic until the polymer hardened at about 220° C.

This polymer had an enantiotropic anisotropic range of 80° C., as opposed to a monotropic anisotropic range of 7° C. for the corresponding nonfluorinated polymer. The anisotropic state for the fluorinated polymer was in a more highly ordered smectic state, as compared to the nematic anisotropic state of the nonfluorinated polymer.

EXAMPLE 53

Preparation of Partially Fluorinated Liquid Crystalline Polyester Copolymer (A)

4,4'-diacetoxybenzoyl phenol (2.00 g), tetrafluorosuberic acid (1.91 g), and 0.01 g calcium acetate were placed in a small polymer tube with a side arm. The resulting mixture was heated to 250° C. and nitrogen was slowly purged through the resulting melt for about 18 hours. The melt was cooled to give an off-white polymer. Fibers could be pulled from the melt. The polymer melted at 215° C. to an anisotropic phase. It remained anisotropic upon heating to 400° C. This yielded an anisotropic range of greater than 185° C., as compared to the nonfluorinated polymer, which had an anisotropic range of 115° C.

Part C

In this part of the Examples section, there is disclosed and taught the preparation of additional dioxolanes according to the invention. Specifically, this part includes amine functionalized dioxolanes and polymers of them.

EXAMPLE 54

Preparation of 2,2-Bis(Trifluoromethyl)-4,5-Di(3-Aminopropyl)-4,5-Difluoro—1,3-Dioxolane In a 1400 ml Hastelloy-C Shaker tube was charged the 2,2-bis(trifluoromethyl)-4,5-di(2-cyanoethyl)-4,5-difluoro—1,3-dioxolane of Example 43 (56.3 g, 0.16 mole), tetrahydrofuran (320 ml) and Raney-Cobalt catalyst (14.4 g). The tube was sealed and cool-evacuated. Ammonia (64 g, 3.765 mole) was transferred into the tube and the tube was pressurized with hydrogen gas to 500 psi. The tube was then heated to 110° C. and the hydrogen pressure was adjusted to 1500 psi. The heating was continued for 18 hrs at this temperature. After the tube was cooled, the product mixture was filtered to remove the catalyst, and solvent was removed in vacuo. The residue was distilled to give the desired product 46 g (80% yield) as a clear, colorless, viscous liquid, Bp. 80° C./0.06 mmHg. H-1 NMR (CDCl$_3$): 3.02 (m, 4H), 2.30 (m, 4H), 1.97 (m, 4H), 1.50 (s, br, —NH$_2$); F-19 NMR (CDCl$_3$): −80.5 (m, 6F), [−108.8 (m, br, trans), −110.6 (m, br cis) (2F total)].

EXAMPLE 55

Preparation of 2,2-Bis(Trifluoromethyl)-4,5-Divinyl-1,3-Dioxolane 2,3-Divinylethylene oxide was prepared according to E. L. Stogryn et al., *J. Org. Chem.*, 29, 1275 (1964). This compound (60 g, 0.625 mole) was mixed with d-limonene (2 g), tetra-n-butylammonium bromide (0.6 g), water (0.6 g) and hexafluoroacetone (108 g, 0.65 mole) in a 360 ml Shaker tube. The tube was sealed and was heated at 80° C./1 h4, 100° C./1hr and 120° C./6 hrs. The product mixture unloaded from the tube was distilled to give the desired product 30 g as a clear, colorless liquid. Bp. 50° C./30 mmHg. The structure was supported by its NMR spectroscopic data.

EXAMPLE 56

Preparation of 2,2-Bis(Trifluoromethyl)-4,5-Di(2—Cyanoethyl)—1,3-Dioxolane

A reaction mixture comprised of Ni(TPP)$_4$ (3.4 g), TTP (2.1 g), toluene (25 ml), 25% EtAlCl$_2$/toluene (1.8M, 2.0 ml) and the compound of Example 55 (24 g, 0.092 mole) was treated at 60° C. with a 50% HCN/toluene solution at 1.5 ml/hr for 4.5 hrs and then 0.5 ml/hr until a gas chromatography showed complete conversion to the dinitrile. The mixture was cooled and a white solid was formed. The solid was collected by filtration and was dissolved in acetonitrile, washed with hexanes, after drying over magnesium sulfate, the solvent was removed and the residue was recrystallized from methanol. 10 g of the desired product was obtained. Mp. 58° to 59.5° C. H-1 NMR (CDCl$_3$): 2.06 (s, br, 4H), 2.64 (s, Br, 4H), 4.20, 4.70 (2s, br, 2H); F-19 NMR (CDCl$_3$): −81.0 (s, br) and −80.2, −80.4 (2s, br).

EXAMPLE 57

Preparation of 2,2-Bis(Trifluoromethyl)-4,5-Di(3-Aminopropyl)-1,3-Dioxolane

The compound of Example 56 (9.72 g, 0.031 mole) was mixed with tetrahydrofuran (60 ml), Raney-Cobalt (2.8 g) and ammonia (12 g, 0.706 mole) in a 360 ml Hastelloy-C Shaker tube. The tube was pressurized with hydrogen to 500 psi at room temperature. The tube was then heated at 110° C. for 18 hrs while the hydrogen pressure was adjusted to 1500 psi under the reaction process. The product mixture was filtered first, then was distilled to give the desired product 4.3 g as a clear, colorless liquid. Bp 85° C./0.02 mmHg. H-1 NMR (CDCl$_3$): 3.98 (s, br, 2H), 2.76 (t, J=6 Hz, 4H), 1.80−1.50 (m, 8H), 1.30 (s, br, 4H); F-19 NMR (CDCl$_3$): −81.1 (s, 6F).

EXAMPLE 58

Preparation of a Polyimide from PMDA(1,2,4,5-Benzenetetracarboxylic Anhydride) by Chemical Imidization Method In a dried flask was charged the compound of Example 54 (1.8 g, 0.005 mole) in 1-methyl-2-pyrrolidinone (NMP) (18 g) solvent. The mixture was stirred until all the compound was dissolved. The solid PMDA (1.09 g, 0.005 mole/ was added under nitrogen atmosphere. The mixture was stirred for 16 hrs at ambient temperature to give a polyamic acid solution.

In a separate flask, a mixture of NMP (10 ml), pyridine (1.08 g, 0.0137 mole) and acetic anhydride (1.28 g, 0.0125 mole) was heated to 100° C. To this solution the polyamic acid solution prepared from above was dripping in slowly. After the addition was complete, the mixture was further stirred for 2 hrs at 100° C. After cooling, the product mixture was poured into water with vigorous stirring. The solid precipitate formed was filtered, washed thoroughly with water and methanol. Then was dried in a vacuum oven (ca. 150 mmHg) at 220° C. for 4 hrs to give a very pale-brown solid polymer (1.71 g). This polymer has shown a Tm at 295° C. as determined by DSC measurement.

EXAMPLE 59

Preparation of a polyimide from 6-FDA[4,4'-Hexafluoroisopropylidene)diphthalic Anhydride] by Thermal Imidization Method The polyamic acid solution was prepared as described above from the compound of Example 54 (1.8 g, 0.005 mole) and 6-FDA (2.22 g, 0.005 mole) in NMP solvent. Half amount of the polyamic acid solution formed was imidized under the following thermal conditions: 100° C./0.5 hr, 150° C./0.5 hr, 200° C./1 hr, 250° C./1 hr and finally 280° C./1 hr. After cooling, 1.37 g solid polyimide was obtained. This polyimide has shown a Tg at 120° C. as measured by DSC. The structure of the polyimide was confirmed by its H-1 and F-19 NMR spectroscopic data.

EXAMPLE 60

Preparation of a Polyimide from ODA-(4,4'-Oxydianiline) (7:3 mole ratio)/PMDA

This polyimide was prepared from the compound of Example 54 (9 g, 0.025 mole), ODA (11.66 g, 0.0583 mole) and PMDA (18.25 g, 0.0833 mole) in N,N-dimethylacetamide (DMAC) solvent (222 g). The resulting film from this polyimide with 41 μm thickness gave a tensile strength 84 MPa, elastic modulus 1200 MPa and 17% elongation.

What is claimed is:

1. Dioxolanes of the formula

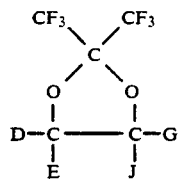

wherein D, E, G and J are:

| D | E | G | J |
|---|---|---|---|
| Cl | I | Cl | Cl |
| Br | H | Br | Cl |
| Br | Cl | Br | Cl |
| F | F | Cl | Cl |
| F | I | F | I |
| F | I | F | Br |
| F | I | F | Cl |
| F | I | F | F |
| F | Br | F | F |
| F | $CH_2CH_2I$ | F | $CH_2CH_2I$ |
| F | $CH_2CH_2I$ | F | F |
| F | $CH_2CH_2I$ | F | Cl |
| F | $CH_2CH_2I$ | F | Br |
| F | $CH=CH_2$ | F | $CH=CH_2$ |
| F | $CH=CH_2$ | F | F |
| F | $CH=CH_2$ | F | Cl |
| F | $CH=CH_2$ | F | Br |
| F | COOH | F | F |
| F | COOH | F | Cl |
| F | COOH | F | Br |
| F | COCl | F | F |
| F | COF | F | F |
| H | $CH=CH_2$ | H | $CH=CH_2$ |
| H | $CH_2CH_2CN$ | H | $CH_2CH_2CN$ |
| H | $CH_2CH_2CH_2NH_2$ | H | $CH_2CH_2CH_2NH_2$. |

* * * * *

UNITED STATES PATENT AND TRADEMARK OFFICE
CERTIFICATE OF CORRECTION

PATENT NO. : 5,233,058
DATED : August 3, 1993
INVENTOR(S) : Douglas R. Anton, et. al.

It is certified that error appears in the above-indentified patent and that said Letters Patent is hereby corrected as shown below:

On the Title page, item [75], inventors: should read--Douglas R. Anton, Claymont; Ming-Hong Hung; Ronald J. McKinney; Paul Raphael Resnick, Wilmington, all of Del.

Signed and Sealed this

Eleventh Day of October, 1994

Attest:

BRUCE LEHMAN

Attesting Officer

Commissioner of Patents and Trademarks